Figure 1:
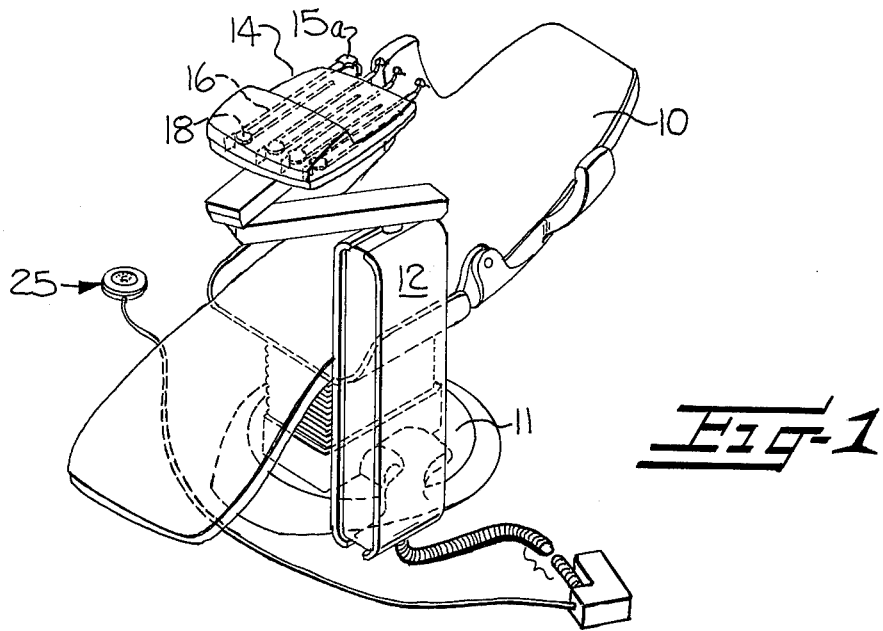

United States Patent [19]

Childress

[11] 4,106,198

[45] Aug. 15, 1978

[54] CONTROL ARRANGEMENT FOR HANDPIECE INSTRUMENT

[75] Inventor: Bobby Belton Childress, Charlotte, N.C.

[73] Assignee: Pelton & Crane Company, Charlotte, N.C.

[21] Appl. No.: 741,385

[22] Filed: Nov. 12, 1976

[51] Int. Cl.$^2$ .............................................. A61C 19/02
[52] U.S. Cl. ....................................................... 32/22
[58] Field of Search ............................ 32/22, DIG. 3; 137/355.2, 355.22, 355.23

[56] References Cited

U.S. PATENT DOCUMENTS

| 3,702,940 | 11/1972 | Stewart | 32/22 |
| 3,778,903 | 12/1973 | Gardella et al. | 32/22 |

Primary Examiner—Robert Peshock
Attorney, Agent, or Firm—Bell, Seltzer, Park & Gibson

[57] ABSTRACT

A plurality of dental, medical or the like handpiece instruments normally housed in one or more instrument consoles and extensible relative thereto for use are controlled by apparatus which assures safety in use of the handpiece instruments and accommodates control over the functioning of a selected one handpiece instrument from a single common foot operated controller. In a particular environment for this invention, as described more fully hereinafter, flexible hose are respectively attached to a plurality of instrument handpieces and are extensible from a console, which receives the plurality of handpieces, upon selection and removal of corresponding ones of the handpiece instruments. Detectors are provided for sensing the removal of each handpiece instrument from the console, and provision is made for selectively delivering at least one of a plurality of fluids through the flexible hose to each of the plurality of handpieces. In accordance with the present invention, control circuitry operatively connected with and responsive to the detectors and to the foot controller is operatively connected with a handpiece locking arrangement and with the fluid supply for identifying a handpiece which has been selected by an operator and removed from the console for use, for enabling the handpiece lock during a predetermined interval of time after selection and removal of any one handpiece instrument to lock any selected handpiece instrument and the respective hose in an extended position, for distinguishing among varying patterns of actuation of the foot controller indicative of selection of a certain fluid for delivery, for enabling delivery of selected fluid to a selected handpiece instrument only, and for disabling the handpiece lock from locking any other handpiece in extended position after the predetermined time interval following selection and removal of a selected handpiece.

12 Claims, 3 Drawing Figures

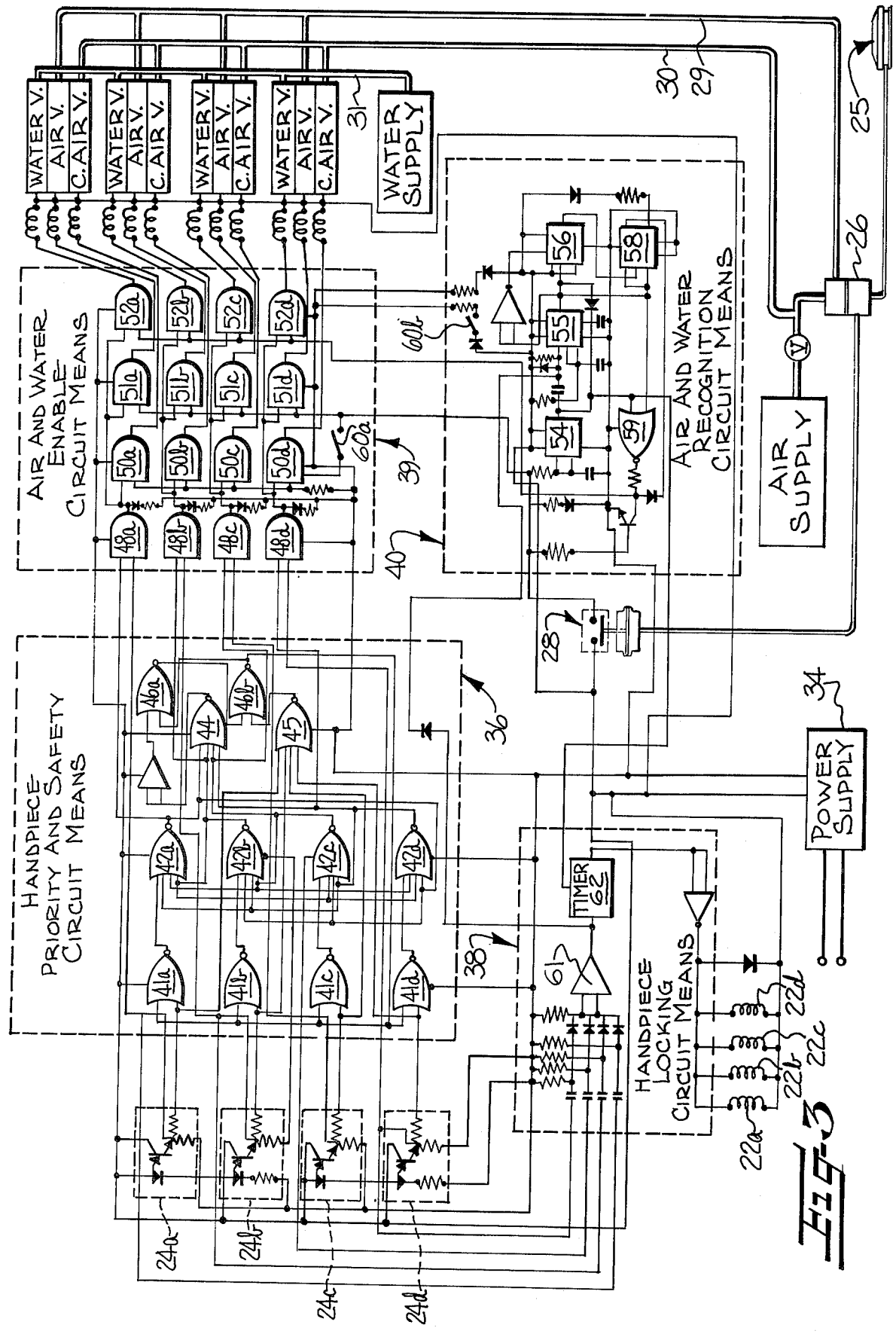

CONTROL ARRANGEMENT FOR HANDPIECE INSTRUMENT

Recent development in dental and surgical techniques has led to use by dentists and physicians of a plurality of handpiece instruments during attendance to any given single patient. Particularly in the instance of dental techniques, such use of a plurality of instrument handpieces or handpiece instruments is determined by the desire of a dentist or dental technician to have a choice among various bits, speeds of bit operation, fluids to be applied during a particular procedure, and the like. One early example of such varying demands for differing instrument handpieces arose from the use of air turbine drills for certain procedures while the older dental engine or low speed drill was the instrument of choice for other procedures. In certain restoration work, for example, reliance would be placed upon use of an air turbine drill at certain stages and on a low speed drill at other stages.

As can be appreciated, the efficiency of a dentist or dental technician and/or any assisting dental technician will be maximized where possible confusion over the specific instrument handpiece subject to operation is avoided. Where a multiplicity of instrument handpieces are available and control arrangements therefore are not unified, the possibility exists that a technician changing a burr or bit in a handpiece believed not selected may be injured in the event that the handpiece is inadvertently or accidentally activated.

Further, the proliferation of instrument handpieces to control can increase the opportunities for confusion, inadvertence or mistake by presenting a dentist or other operator with an equal proliferation of controllers each for its corresponding instrument handpiece or for a subset of several instrument handpieces.

With the above discussion in mind, it is an object of this invention to enhance the efficiency of a dentist or other operator of a plurality of instrument handpieces while simplifying the controllers which need to be operated by the operator and decreasing the risk of accident to the dentist, any assisting technician, and the patient. In realizing this object of the present invention, interconnections among a foot controller, detectors responsive to the selection and removal of a handpiece, a locking arrangement for the handpieces, and a fluid supply arrangement therefor are through a unifying control arrangement. The control arrangement, in accordance with the present invention, is capable of recognizing selection of a particular instrument handpiece and blocking the operation of other handpieces until such time as use of the selected handpiece has ended and the selected handpiece has been restored to a position of non-use.

Yet a further object of this invention is to permit a dentist or other operator using a plurality of instrument handpieces to select fluids to be delivered to a selected one handpiece by actuating a foot controller in varying patterns of actuation determined by the fluid or fluids to be selected for delivery. In realizing this object, the object arrangement of the present invention includes a signal recognition component and a fluid delivery enabling component, interconnected so as to enable delivery of selected fluid to a selected handpiece only in response to selection of the handpiece and distinguishing of a pattern of actuation of a foot controller indicative of selection of the particular fluid.

Yet a further object of this invention is to facilitate the changing or other servicing of instrument handpieces while a selected handpiece is in use. In realizing this object, the control arrangement of the present invention is operatively interconnected with detectors responsive to the selection of a handpiece and handpiece locking devices, so that a selected handpiece may be locked in extended position for use while any nonselected handpiece may be freely extended, locked, and retracted as required for servicing.

Figure 2:
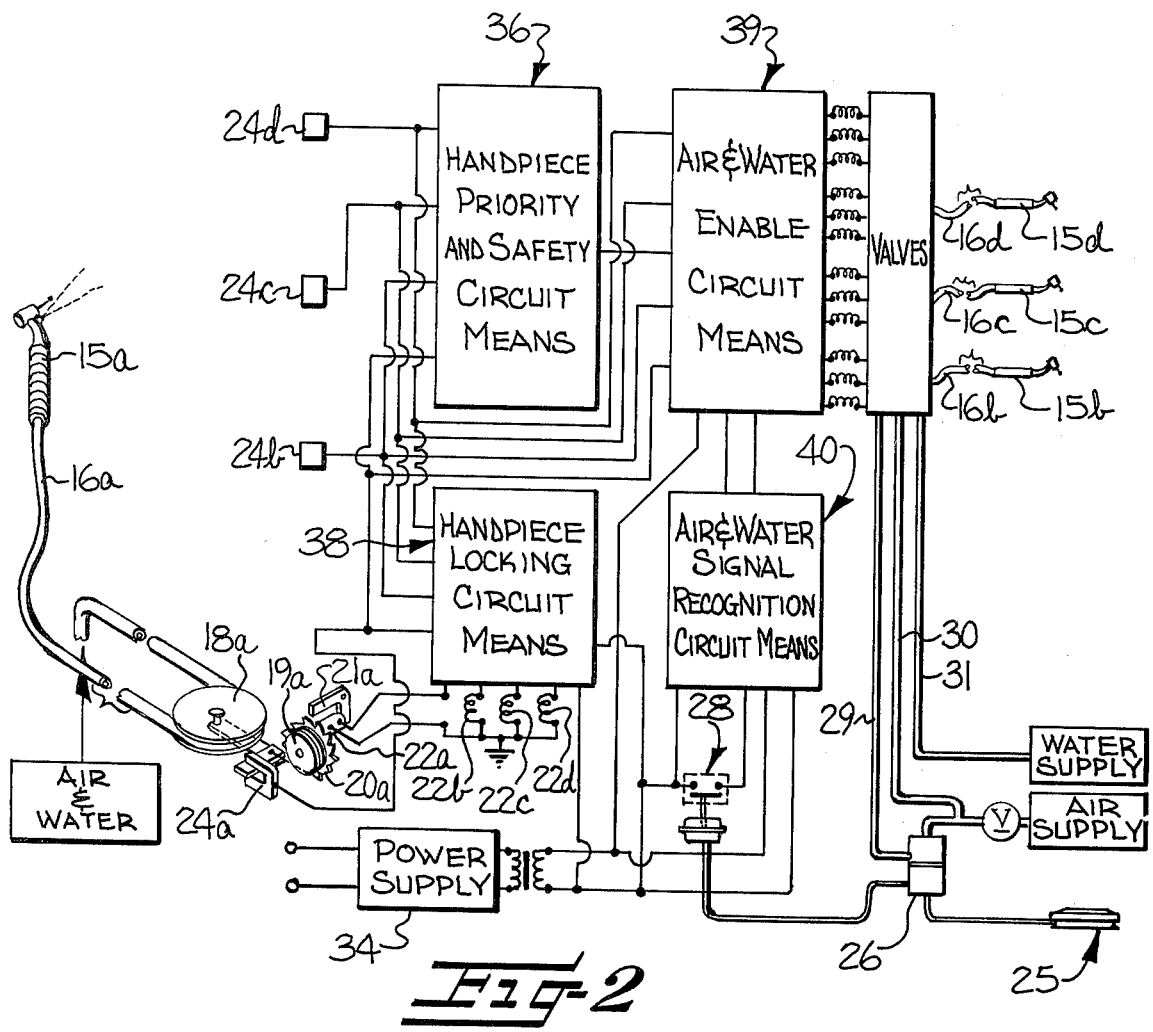

Some of the objects of the invention having been stated, other objects will appear as the description proceeds, when taken in connection with the accompanying drawings, in which FIG. 1 is a perspective view of one environment in which the present invention finds utility;

FIG. 2 is a schematic diagram, largely in block form, showing the control apparatus of the present invention as applied to the environmental setting of FIG. 1; and FIG. 3 is a schematic diagram similar to FIG. 2 but presenting greater detail for certain circuitry elements thereof.

The present invention will be described hereinafter with particular reference to the aforementioned accompanying drawings which illustrate one particular operating embodiment for the present invention. However, it is to be understood at the outset of the following description that both the specific environmental setting and the particular circuitry to be described may be varied by persons skilled in the applicable arts without departing from the true scope contemplated for the present invention. Accordingly, the following description and the drawings to which it refers are to be understood as a broad teaching of the present invention and not as being restrictive upon the true scope of protection to be afforded.

Referring now more particularly to FIG. 1, the environment for the present invention there shown includes a moveable power-operated instrument console and treatment chair apparatus such as is described in copending application Ser. No. 741,381 filed Nov. 12, 1976 and owned in common with the present subject invention. Interested readers are directed to disclosure to be found there or to similar disclosures to be found in prior patents disclosing instrument consoles and treatment chairs. While the present invention is contemplated as having particular advantages when used in the environment provided by the aforementioned related invention, perceptive readers skilled in the appropriate arts will understand the even broader utility of the arrangements to be described hereinafter.

In the illustrated environment, a treatment chair 10 is provided which preferably is movable vertically with respect to a base 11. Adjacent the base 11 is positioned a console 12 having a tray portion 14 positionable above the treatment chair 10. The tray 14 receives a plurality of handpieces, one of which is identified at 15a in FIG. 1. The details of construction of the handpiece 15a may be found by any interested reader in the disclosures of pertinent prior patents. Where appropriate or desirable, a further console (not shown) may be provided which is particularly intended for use by a dental assistant, in accordance with the description to be found in co-pending application Ser. No. 741,366 filed Nov. 12, 1976 and owned in common with the present invention. Thus, it will be appreciated that the plurality of instrument handpieces with which the following description is concerned may be located in one or more consoles.

Referring now more particularly to FIG. 2, only a single handpiece 15a has been there indicated in enlarged detail, in order that greater detail may be shown for other portions more fully characterizing the present invention. As will, however, be appreciated from the illustration of a single handpiece 15a, flexible hose respectively attached to each of the plurality of handpieces received by the tray 14 are provided. That hose specifically supplying the handpiece 15a has been indicated at 16a and preferably, in the environment for this invention, forms a portion of an improved mechanism for extending and retracting flexible hose as described in co-pending application Ser. No. 741,384 filed Nov. 12, 1976 and owned in common with the present subject invention.

As more fully described there, a pulley 18a may be positioned intermediate to the length of a U-shaped flexible hose 16a and be attached to a cable extending from a rotatable reel 19a which in turn carries a ratchet wheel 20a. The ratchet wheel 20a is engageable by a latch pawl 21a such that the instrument 15a and hose 16a may be pulled to an extended position and the pawl 21a engaged with the ratchet wheel 20a to lock the hose and instrument in the extended position for use. As also described there, an electrically energizable latching coil 22a may control the position of the pawl 21a and in turn be controlled by a detector means which senses the removal of the handpiece from the console. In the specific environment illustrated for the present invention, the detector means takes the form of an electro-optical switching arrangement generally indicated at 24a and which will be described in somewhat greater detail hereinafter. Persons skilled in the applicable arts will be able to recognize the possibility of constructing still other electro-mechanical locking or latching arrangements operable with the control arrangement of the present invention as described more fully hereinafter.

Each flexible hose, such as the hose 16a has the capability of delivering selected fluid to the corresponding handpiece, such as the handpiece 15a. Fluid may be selected from among one or more types and may serve one or more functions. By way of example, air may be delivered through the hose 16a to the handpiece 15a for driving a turbine. Such air is commonly referred to as turbine drive air or main air. Air may also be delivered for blowing against a burr or a tooth surface being operated upon for the purpose of removing chips. Such an air flow is commonly referred to as chip air. Additionally, water may be delivered to provide a water spray against a burr and a tooth surface being operated upon. As will be appreciated by persons skilled in the applicable arts, chip air and water may be called for or desired selectively, depending upon the particular technique preferred by an individual operator.

Foot controller apparatus including a pedal device generally indicated at 25 is provided in order that a dentist or technician operating the handpieces may govern the operation thereof. In the particular environment shown for the present invention, the foot controller apparatus takes the form more fully described in co-pending application Ser. No. 741,383 filed Nov. 12, 1976 and owned in common with the present invention. In that specific environment, a pedal device is located remotely from an air regulator indicated generally at 26 (FIG. 2) and an air operated electrical switching device 28. Exertion of foot pressure against the device 25 governs the flow of air and thus the air pressure delivered through the regulator 26 and additionally governs the conductance of electricity through the switch 28. Regulated air pressure delivered through the regulator 26 is available for use as main air and thus accomplishes control over the rotational speed of a turbine driven drill such as may be found in handpiece 15a. Such main air is delivered from the regulator 26 through an appropriate conduit 29 to a bank of electrical solenoid control valves (described more fully hereinafter) for delivery to a selected handpiece. Similarly, chip air is delivered through a conduit 30 and water is delivered through a conduit 31 to the bank of solenoid operated valves which function as a supply means for selectively delivering at least one of a plurality of fluids through flexible hoses to each of the plurality of handpieces.

In accordance with the present invention, control apparatus means are operatively connected with and responsive to the detector means 24a and the foot controller switch 28 and are operatively connected with the locking coil 22a of the handpiece locking means and with the solenoid operated valves of the supply means. The control apparatus means, preferably in the form of an electrical circuit arrangement using semi-conductor devices, identifies a handpiece 15a which has been selected by an operator and removed from the console tray 14 for use, enables the handpiece locking means for a predetermined time interval ater selection and removal of any one handpiece to lock any selected handpiece and the respective hose in extended position, distinguishes among varying patterns of actuation of the foot controller switch 28 indicative of selection by an operator of certain fluids for delivery, enables delivery of a selected fluid through the applicable one of the solenoid valves receiving fluid from the conduits 29, 30, 31, and disables the handpiece locking means from locking any other handpiece in extended position.

The control apparatus of the present invention will be first described with reference to certain subsystems and the functions thereof, with more specific detail of one manner of constructing such sub-systems being pointed out subsequently in the description which follows. Referring now more particularly to FIG. 2, an embodiment of this invention in which the control arrangements are primarily electronic is powered by an appropriate power supply 34. The electronic control circuitry includes a handpiece priority and safety circuit means 36 electrically connected with handpiece responsive switches for each of the plurality of instrument handpieces to be made subject to the control apparatus, such as the switch 24a for the handpiece 15a. The switches are additionally connected with a handpiece locking circuit means 38 and an air and water enable circuit means 39. The air and water enable circuit means is additionally connected with an air and water signal recognition circuit means 40 as well as to the solenoid valves controlling operative communications between the supply conduits 29, 30, 31 and the various handpieces.

Turning now to the operation and interrelationships of the components of the control apparatus in accordance with the present invention, selection of any particular handpiece, such as the handpiece 15a, by a dentist, dental assistant or other operator causes a change in conductive state of the corresponding handpiece responsive switch 24a. In accordance with the illustrated embodiment of the present invention, emission of such an electrical signal supplies input signals for the handpiece priority and safety circuit means 36, the handpiece locking circuit means 38, and the air and water enable circuit means 39. Such an input signal to the handpiece priority and the circuit means results in a first actuating signal being sent to the air and water enable circuit means, indicating that solenoid valves may be energized to pass selected fluid to the handpiece 15a. Additionally, the handpiece priority and safety circuit means recognizes the first handpiece removed after all handpieces are in rest position in the console tray 14 as being the handpiece to which priority is to be given. Thereafter, the handpiece priority and safety circuit means 36 precludes emission of an actuating signal to the air and water enable circuit means 39 until such time as all handpieces have been restored to the rest positions within the console tray 14. That is, a first actuating signal cannot again be emitted until such time as all handpieces have been restored and a handpiece has again been selected and removed. Thus, the handpiece priority and safety circuit means 36 will be understood as assuring no inadvertent transfer of a control from one handpiece to another.

When the handpiece locking circuit means 38 has been signalled that any handpiece has been selected and removed, all handpiece latching coils 22a, 22b, 22c, 22d are energized for a predetermined period of time, permitting all latching pawls to fall onto the corresponding ratchet wheels. Thus, all handpieces are enabled to be latched in accordance with the disclosure of the aforementioned related invention for a predetermined interval of time. After that predetermined interval of time, the handpiece locking circuit means 38 energizes all handpiece latching coils thus disabling the handpiece locking arrangements from locking any other handpiece in extended position after the predetermined time interval.

The air and water signal recognition circuit means is operatively connected with the foot controller switch 28 for receiving therefrom electrical signals indicative of actuation of the pedal device 25. More particularly, closure of the switch 28 is recognized by the signal recognition circuit means 40 as calling for enablement of delivery of certain selected fluids, while patterns of successive opening and closing of the switch means 28 are recognized as selecting other fluids or combinations of fluids for delivery. Thus, the signal recognition circuit means 40 is effective for forwarding to the air and water enable circuit means a second actuating signal indicative of specific types of valves to be energized.

Upon receipt at the air and water enable circuit means of the first and second actuating signals as well as a signal indicative of the specific handpiece selected, solenoid valves specific to the selected handpiece and to the selected fluids are energized so as to admit fluid from the appropriate one or more of the conduits 29, 30, 31 to the selected hose 16a, 16b, 16c, 16d for delivery to the respective handpiece.

Referring now more specifically to FIG. 3, one operating embodiment of the control arrangement of the present invention relies upon handpiece responsive switches while use light emitting diodes (LEDs) optically coupled with phototransistors. Each phototransistor of the plurality of handpiece responsive switches is electrically connected with a corresponding one of a plurality of NOR gate devices 41a, 41b, 41c, 41d. Each of these gate devices is electrically connected to receive as a second input a signal indicative that the handpiece priority and safety circuit means 36 has forwarded the first actuating signal to the air and water enable circuit means 39 in a manner such as to block passage of a second or subsequent signal originating from a handpiece responsive switch by switching all but one gate device to a "don't care" state. More particularly, each of the gate devices 41a through 41d is electrically connected with a corresponding one of a series of multiple input NOR gates 42a, 42b, 42c, 42d. Each of the multiple input NOR gates 42a through 42d forwards an appropriate electrical signal to the air and water enable circuit means 39 and additionally to one of a pair of multiple input NOR gates 44, 45 which are connected to drive a pair of interconnected gates 46a, 46b functioning as a set-reset flip-flop or bistable multivibrator. One multivibrator drive gate 44 is connected to receive signals from the NOR gates 42a through 42d, while the other drive gate 45 is connected to receive signals from the handpiece responsive switches 24a through 24d. The multivibrator 46a, 46b when set "remembers" that one of the handpiece responsive switches 24a through 24d has become conductive and establishes priority for that one handpiece by feeding back the first actuating signal to the first series of gate devices 41a through 41d as described above. The multivibrator 46a, 46b is reset and "forgets" after all handpieces being restored to non-use position and a handpiece is subsequently selected.

As will be noted, the first actuating signal emitted from the handpiece priority and safety circuit means 36 is applied to the appropriate one of a series of decoding AND gate devices 48a, 48b, 48c, 48d forming portions of the air and water enable circuit means 39. The appropriate one of these gate devices 48a through 48d will additionally have applied thereto a signal originating from the corresponding handpiece responsive switch, thereby enabling the selected one gate to deliver an output signal to a matrix of following water AND gate devices 50a through 50d, chip air AND gate devices 51a through 51d, and main air AND gate devices 52a through 52d. The function of the handpiece priority and safety circuit means 36, in this context, is to preclude the application of the first actuating signal to any other than one selected one of the decoding gate devices 48a through 48d in such a manner that the appearance of a handpiece responsive switch signal at any other of the decoding gate devices 48a through 48d will not be effective to pass a signal through any such nonselected gate device.

Referring now more particularly to the air and water signal recognition circuit means 40, it is recognized that the actuation of the pedal device 25 by a dentist or other operator may not be entirely smooth and that the mechanical contacts of the switch 28 are subject to less than optimal electrical operation. Accordingly, signals from the switch 28 are passed through an appropriate semiconductor device 54 for providing an optimal signal. Such a signal is applied to a timer device 55, set for a predetermined interval of time such as at least about 0.75 second. As pointed out more fully hereinafter, signals emitted from the input device 54 and the timer device 55 are applied to a pair of bistable multivibrators or flip-flops 56, 58 and to a gate device 59. More particularly, the passage of a signal through the input device 54 begins the timing of the predetermined period such as 0.75 second and results in passage of an initial pulse through the timer device 55 to one multivibrator 56. Should the signal continue until the predetermined time interval has been timed out or completed, the signal passing through the timer 55 to the one multivibrator device 56 is dropped and the set or reset state of the other multivibrator device 58 is not changed from its prior existing state.

In the event that the signal passing through the input device 54 of the recognition circuit means 40 is interrupted prior to timing out of the predetermined time period and is then restored, the multivibrator device 56 is first set to a second state and then passes a signal through to the other multivibrator device 58, which changes that device to the opposite state from its prior state. The other multivibrator device 58 thus functions as a memory in that it changes state (and selected fluid) only on a conscious action by the dentist or operator.

As will be appreciated, a second actuating signal is applied to the enable circuit means 39 in a manner which reflects the memory condition or state of the other multivibrator device 58. In the event that device is set for selection of water and air, the signal is applied to all of the gate devices 50a through 50d, 51a through 51d and 52a through 52d in the matrix and which control the energization of valves for main air, chip air and water. Selection of main air only or of both main and chip air is made by the dentist or other operator manually opening and closing a chip air selection switch 60a, 60b. Should the chip air selection switch 60a, 60b be open then no signal is passed to the chip air gate devices 50a through 50d and no chip air is enabled. In the event that the other multivibrator device 58 is set for selection of air only, no signal is passed through the gate device 59 and thus no second actuating signal reaches any of the water gate devices 52a through 52d in the matrix of the air and water enable circuit means 39.

Selection of air only permits a dentist or other operator to employ chip air through a handpiece in a manner similar to a blowing syringe. That is, actuating the pedal device 25 with a very gentle touch will close the switching device 28 and enable delivery of chip air. However, such actuation can be sufficiently gentle as to cause the flow of air delivered through the regulator 26 to be so low as to not operate a turbine driven bit. The resultant flow of chip air without driving of a bit causes the handpiece to function as a blowing syringe.

As pointed out hereinabove, the handpiece responsive switches 24a through 24d are additionally interconnected with the handpiece locking circuit means 38. As indicated in FIG. 3, an appropriate gate device 61 is connected with all of the handpiece responsive switches 24a through 24d in order to actuate a timer 62 upon any of the handpiece responsive switches changing conductive state. The timer 62 is also responsive to closure of the switching device 28 operated by the pedal device 25. Upon actuation of the timer 62, the handpiece latching coils 22a through 22d are deenergized for a predetermined time interval in the range of from about 1.0 seconds to about 2.0 seconds and preferably 1.10 to 1.25 seconds, so as to permit latching of any withdrawn handpiece in the extended position as described more particularly in the aforementioned related application.

While the control arrangement of this invention has been described hereinabove with particular reference to semiconductor devices as indicated more particularly in FIG. 3, it is acknowledged that skilled electronic designers may employ semiconductor devices of other types in accomplishing the functions ascribed to components in the block diagram of FIG. 2. Accordingly, it is contemplated that persons skilled in the applicable electronic arts may depart from the specific details of FIG. 3 while achieving functional operations consistent with those contemplated by the present invention.

In the drawings and specification, there has been set forth a preferred embodiment of the invention, and although specific terms are employed, they are used in a generic and descriptive sense only and not for purposes of limitation.

That which is claimed is:

1. In an apparatus having a plurality of instrument handpieces, console means for receiving the plurality of handpieces, flexible hose means respectively attached to the handpieces and extensible from the console means upon selection and removal of corresponding ones of the plurality of handpieces from the console means, detector means for sensing the removal of each handpiece from the console means, handpiece locking means operatively associated with the respective flexible hose means for locking the hose means and handpiece in extended position, supply means for selectively delivering at least one of a plurality of fluids through the flexible hose means to each of the plurality of handpieces, and foot controller means actuatable for governing the delivery of fluid to the handpieces; the combination therewith of a control apparatus comprising: means operatively connected with and responsive to the detector means and the foot controller means and operatively connected with the handpiece locking means and the supply means (a) for identifying a handpiece which has been selected by an operator and removed from the console means for use, (b) for enabling the handpiece locking means for a predetermined time interval after selection and removal of any handpiece to lock any handpiece and the respective hose means in extended position, (c) for distinguishing among varying patterns of actuation of the foot controller means indicative of selection of certain fluid for delivery, (d) for enabling delivery of selected fluid to a selected handpiece only, and (e) for disabling the handpiece locking means from locking any other handpiece in extended position after the predetermined time interval.

2. Apparatus according to claim 1 wherein said control apparatus comprises a plurality of interconnected gate devices defining handpiece priority and safety means and fluid signal recognition means and fluid enable means, said handpiece priority and safety means responding to sensed removal of a handpiece from the console means by generating a first actuating signal indicative of the handpiece selected and by blocking generation of a subsequent first actuating signal until return of all handpieces to the console means, said fluid signal recognition means responding to actuation of the foot controller means by generating a second actuating signal indicative of the fluid selected, and said fluid enable means responding to said first and second actuating signals by enabling delivery of the selected fluid to the selected handpiece.

3. Apparatus according to claim 2 wherein said fluid enable means comprises a matrix of gate devices each responsive to corresponding ones of said detector means, said first actuating signals and said second actuating signals.

4. Apparatus according to claim 1 wherein said control apparatus comprises timer means operatively connected with said detector means and said handpiece locking means and responsive to said detector means for enabling locking of all the handpieces upon removal of any handpiece for a determinable time period within the range of from at least about 1.0 seconds to at least about 2.0 seconds.

5. Apparatus according to claim 1 wherein said control apparatus comprises interconnected timer means and counter means operatively connected with said foot controller means for timing a predetermined time period and for counting actuations of said foot controller means within said time period, said control apparatus responding to counting a predetermined numbers of actuations by registering the selection of certain fluid for delivery.

6. In an apparatus having a plurality of instrument handpieces, console means for receiving the plurality of handpieces, flexible hose means respectively attached to the handpieces and extensible from the console means upon selection and removal of corresponding ones of the plurality of handpieces from the console means, detector means for electrically signalling the removal of each handpiece from the console means, handpiece locking means operatively associated with the respective flexible hose means and electrically operable for locking the hose means and handpiece in extended position, supply means including electrically operable valve means for selectively delivering at least one of a plurality of fluids through the flexible hose means to each of the plurality of handpieces, and foot controller means actuatable for governing the delivery of fluid to the handpieces and including electrical switch means; the combination therewith of a control apparatus comprising: means including electrical gate means operatively connected with and responsive to the detector means and the foot controller switch means and operatively connected with the handpiece locking means and the supply means (a) for electrically signalling the identity of a handpiece which has been selected by an operator and removed from the console means for use, (b) for changing the electrical energization of the handpiece locking means to enable for a predetermined time interval after selection and removal of any handpiece the locking of any handpiece and the respective hose means in extended position, (c) for distinguishing among varying patterns of closure of the foot controller switch means indicative of selection of certain fluid for delivery, (d) for energizing said valve means to enable delivery of selected fluid to a selected handpiece only, and e) for disabling the handpiece locking means from locking any other handpiece in extended position after the predetermined time interval.

7. Apparatus according to claim 6 wherein said control apparatus comprises a matrix of interconnected gate devices responsive to the detector means and to one another for generating an actuating signal identifying the first handpiece selected and removed from the console means and for blocking generation of the next subsequent actuating signal until return of all handpieces to the console means.

8. In an apparatus having a plurality of instrument handpieces, console means for receiving the plurality of handpieces, flexible hose means respectively attached to the handpieces and extensible from the console means upon selection and removal of corresponding ones of the plurality of handpieces from the console means, detector means for sensing the removal of each handpiece from the console means, supply means for selectively delivering at least one of a plurality of fluids through the flexible hose means to each of the plurality of handpieces, and foot controller means actuatable for governing the delivery of fluid to the handpieces; the combination therewith of a control apparatus comprising: means operatively connected with and responsive to the detector means and the foot controller means and operatively connected with the supply means (a) for identifying a handpiece which has been selected by an operator and removed from the console for use, (b) for distinguishing among varying patterns of actuation of the foot controller means indicative of selection of certain fluid for delivery, and (c) for enabling delivery of selected fluid to a selected handpiece only.

9. In an apparatus having a plurality of instrument handpieces, console means for receiving the plurality of handpieces, flexible hose means respectively attached to the handpieces and extensible from the console means upon selection and removal of corresponding ones of the plurality of handpieces from the console means, detector means for electrically signalling the removal of each handpiece from the console means, supply means including electrically operable valve means for selectively delivering at least one of a plurality of fluids through the flexible hose means to each of the plurality of handpieces, and foot controller means actuatable for governing the delivery of fluid to the handpieces and including electrical switch means; the combination therewith of a control apparatus comprising: means including electronic gate devices operatively connected with and responsive to the detector means and the foot controller switch means and operatively connected with the supply means (a) for electrically signalling the identity of a handpiece which has been selected by an operator and removed from the console for use, (b) for distinguishing among varying patterns of closure of the foot controller switch means indicative of selection of certain fluid for delivery, and (c) for energizing said valve means to enable delivery of selected fluid to a selected handpiece only.

10. In an apparatus having a plurality of instrument handpieces, console means for receiving the plurality of handpieces, flexible hose means respectively attached to the handpieces and extensible from the console means upon selection and removal of corresponding ones of the plurality of handpieces from the console means; detector means for sensing the removal of each handpiece from the console means, and handpiece locking means operatively associated with the respective flexible hose means for locking the hose means and handpiece in extended position; the combination therewith of a control apparatus comprising: means operatively connected with and responsive to the detector means and operatively connected with the handpiece locking means (a) for identifying a handpiece which has been selected by an operator and removed from the console for use, (b) for enabling the handpiece locking means for a predetermined time interval after selection and removal of any handpiece to lock any handpiece and the respective hose means in extended position and (c) for disabling the handpiece locking means from locking any other handpiece in extended position after expiration of the predetermined time interval.

11. In an apparatus having a plurality of instrument handpieces, console means for receiving the plurality of handpieces, flexible hose means respectively attached to the handpieces and extensible from the console means upon selection and removal of corresponding ones of the plurality of handpieces from the console means; detector means for electrically signalling the removal of each handpiece from the console means, and handpiece locking means operatively associated with the respective flexible hose means and electrically operable for locking the hose means and handpiece in extended position; the combination therewith of a control apparatus comprising: means including electronic timer and gate devices operatively connected with and responsive to the detector means and operatively connected with the handpiece locking means for timing a predetermined interval after a handpiece has been selected by an operator and removed from the console for use, changing the electrical energization of the handpiece locking means during said predetermined time interval after selection and removal of any handpiece to lock any handpiece and the respective hose means in extended position, and for disabling the handpiece locking means from locking any handpiece in extended position after expiration of said predetermined time interval.

12. Apparatus according to claim 8 wherein said control apparatus comprises interconnected timer means and counter means operatively-connected with said foot controller means for timing a predetermined time period and for counting actuations of said foot controller means within said time period, said control apparatus responding to counting of a predetermined number of actuations by registering the selection of certain fluid for delivery.

UNITED STATES PATENT AND TRADEMARK OFFICE
CERTIFICATE OF CORRECTION

PATENT NO. : 4,106,198

DATED : August 15, 1978

INVENTOR(S) : Bobby Belton Childress

It is certified that error appears in the above-identified patent and that said Letters Patent are hereby corrected as shown below:

Column 1, Line 62, delete "object" and insert --control--;
Column 4, Line 26, change "ater" to --after--; Column 5,
Line 59, delete "while" and insert --which--; Column 6,
Line 57, change "hereinafater" to --hereinafter--;
Column 9, Line 7, delete "a" and insert --of--; Column 9,
Line 43, change "e)" to --(e)--.

Signed and Sealed this

Thirteenth Day of March 1979

[SEAL]

Attest:

RUTH C. MASON
*Attesting Officer*

DONALD W. BANNER
*Commissioner of Patents and Trademarks*